United States Patent
Kim et al.

(10) Patent No.: US 10,683,251 B2
(45) Date of Patent: Jun. 16, 2020

(54) APPARATUS AND METHOD FOR PREPARING BISPHENOL A

(71) Applicant: LG CHEM, LTD., Seoul (KR)

(72) Inventors: Tae Woo Kim, Daejeon (KR); Sung Kyu Lee, Daejeon (KR); Joon Ho Shin, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/565,047

(22) Filed: Sep. 9, 2019

(65) Prior Publication Data

US 2020/0017431 A1     Jan. 16, 2020

Related U.S. Application Data

(62) Division of application No. 15/769,599, filed as application No. PCT/KR2016/013405 on Nov. 21, 2016, now Pat. No. 10,442,746.

(30) Foreign Application Priority Data

Nov. 19, 2015    (KR) ........................ 10-2015-0162479

(51) Int. Cl.
| | |
|---|---|
| *C07C 37/84* | (2006.01) |
| *B01D 9/00* | (2006.01) |
| *C07C 39/16* | (2006.01) |
| *C07C 37/68* | (2006.01) |
| *B01L 9/00* | (2006.01) |

(52) U.S. Cl.
CPC ................ *C07C 37/84* (2013.01); *B01D 9/00* (2013.01); *B01D 9/0059* (2013.01); *B01L 9/00* (2013.01); *C07C 37/685* (2013.01); *C07C 39/16* (2013.01); *Y02P 20/124* (2015.11)

(58) Field of Classification Search
CPC ....... C07C 37/84; C07C 37/685; C07C 39/16; B01D 9/0059
USPC ........................................................ 422/187
See application file for complete search history.

(56) References Cited

U.S. PATENT DOCUMENTS

| | | |
|---|---|---|
| 5,198,591 A | 3/1993 | Kiedik et al. |
| 5,345,000 A | 9/1994 | Moriya et al. |
| 2016/0159716 A1 | 6/2016 | Park et al. |

FOREIGN PATENT DOCUMENTS

| | | |
|---|---|---|
| JP | 2003-160524 A | 6/2003 |
| JP | 2005-330188 A | 12/2005 |
| JP | 2006-008634 A | 1/2006 |
| JP | 2006-036668 A | 2/2006 |
| KR | 10-2006-0126403 A | 12/2006 |
| KR | 10-0899496 B1 | 5/2009 |
| KR | 10-2015-0008005 A | 1/2015 |
| WO | 2015005726 A1 | 1/2015 |

*Primary Examiner* — Huy Tram Nguyen
(74) *Attorney, Agent, or Firm* — Dentons US LLP

(57) ABSTRACT

The present application relates to a bisphenol A preparation apparatus and preparation method, and provides a bisphenol A preparation apparatus and preparation method, which can increase the overall energy efficiency of a process by using an internal heating source.

17 Claims, 2 Drawing Sheets

[Figure 1]
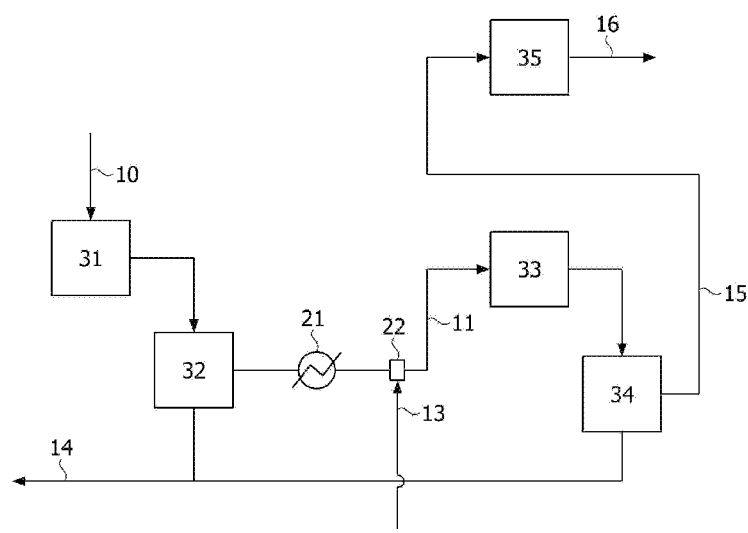
[Figure 2]
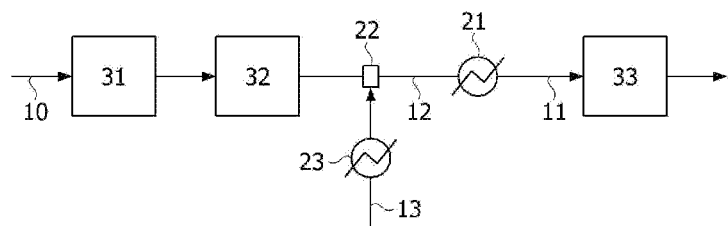

[Figure 3]
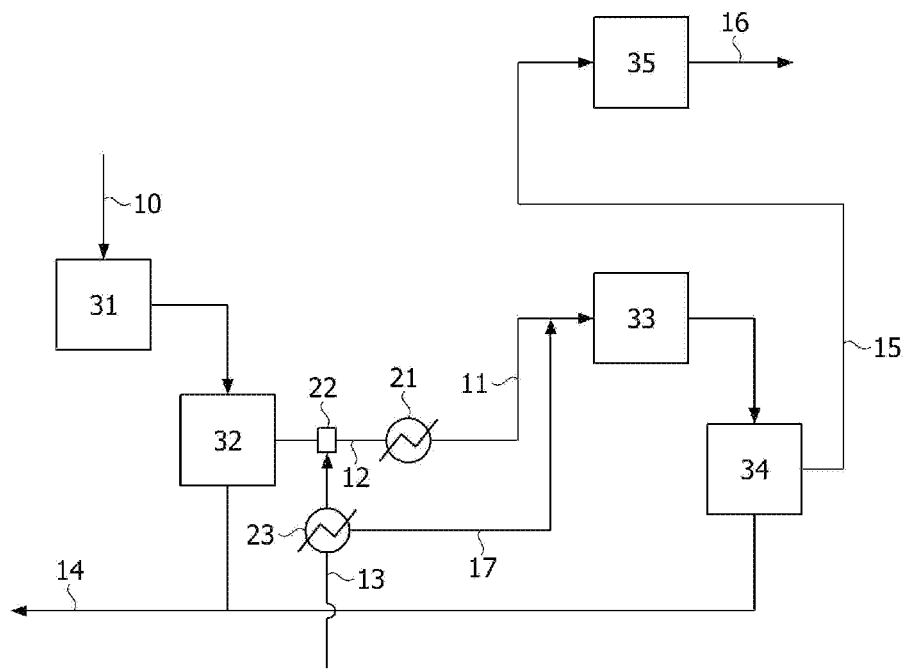
[Figure 4]
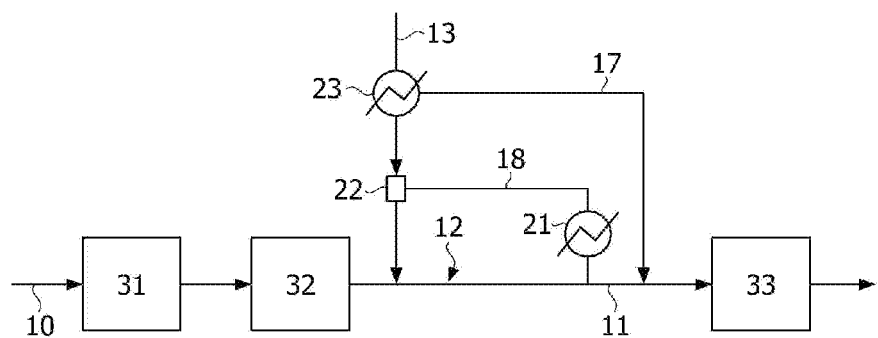

us 10,683,251 B2

APPARATUS AND METHOD FOR PREPARING BISPHENOL A

CROSS-REFERENCE TO RELATED APPLICATIONS

This application is a Divisional of U.S. patent application Ser. No. 15/769,599, filed on Apr. 19, 2018, now is U.S. patent Ser. No. 10/442,746, which is the U.S. National Phase application of International Application No. PCT/KR2016/013405, filed on Nov. 21, 2016, which claims the benefit of Korean Patent Application No. 10-2015-0162479, filed on Nov. 19, 2015, all of which are hereby incorporated by reference in their entirety for all purposes as if fully set forth herein.

TECHNICAL FIELD

Technical Field

The present application relates to an apparatus and a method for preparing bisphenol A.

Background Art

Bisphenol A is prepared by reacting an excess amount of phenol with acetone in the presence of an acid catalyst. In order to obtain high purity bisphenol A from this reaction product, low-boiling substances including water are removed and solid addition product crystals of bispenol A and/or bisphenol A and phenol are precipitated by crystallization treatment, the solid addition product containing slurry is subjected to solid-liquid separation, and then phenol is removed from the recovered solid addition product to obtain bisphenol A.

In order to efficiently purify a large volume of reactants industrially, a continuous crystallization method has been used. In the continuous crystallization method, the solid addition product containing suspension (slurry) obtained in a crystallizer is subjected to solid-liquid separation, so that the solid addition product is recovered and the liquid phase portion remains. Since the liquid phase portion includes about 70 wt % of phenol, about 15 wt % of bisphenol A, and the remaining other by-products, the reaction mother liquid passing through a process of removing some by-products has been circulated and supplied to a reactor requiring an excessive amount of phenol, in order to recycle the phenol contained in the liquid phase portion. Furthermore, by removing phenol from the solid addition product, the bisphenol A is purified and obtained. In this process, there is a need to increase the process efficiency.

PRIOR ART DOCUMENTS

Patent Documents

1. Korean Patent No. 0899496

DISCLOSURE

Technical Problem

The present application provides an apparatus for preparing bisphenol A and a preparation method thereof that can increase the reaction efficiency of the entire process by utilizing internal energy and can save energy.

Technical Solution

The present application relates to an apparatus for preparing bisphenol A. FIGS. 2 to 4 are process diagrams of an exemplary apparatus for preparing bisphenol A according to the present application. In one example, the apparatus for preparing bisphenol A may comprise a first crystallizer (31) to which a bisphenol A concentration stream (10) containing a reaction product that phenol and acetone are reacted is introduced to crystallize bisphenol A and to discharge an adduct of crystallized bisphenol A and phenol; a first solid-liquid separator (32) in which the adduct of crystallized bisphenol A and phenol in the first crystallizer (31) is introduced thereto, and separated from a mother liquid and discharged; a phenol introduction port (22) in which a phenol stream (13) is introduced into the adduct of crystallized bisphenol A and phenol discharged from the first solid-liquid separator (32) to discharge the mixed stream (12) of phenol with the adduct of crystallized bisphenol A and phenol; a first heat exchanger (23) in which the phenol stream (13) is heated before the phenol stream (13) is introduced; a second heat exchanger (21) in which the adduct of crystallized bisphenol A and phenol in the mixed stream (12) flowing out to the phenol introduction port (22) is melted to discharge the molten stream (11); and a second crystallizer (33) to which the molten stream (11) discharged from the second heat exchanger (21) is introduced to recrystallize bisphenol A and to discharge the adduct of crystallized bisphenol A and phenol. The production apparatus according to the present application can mix low-temperature phenol with the addition of crystallized bisphenol A and phenol through the phenol stream (13). In the apparatus for preparing according the present application, low-temperature phenol may be mixed with the adduct of crystallized bisphenol A and phenol through the phenol stream (13). The low temperature phenol may serve to lower the melting point of a substance to be melted by being mixed with the crystallized product before the crystallized product is melted into the molten stream (11). Accordingly, the present application can utilize the low temperature heat source of phenol. That is, conventionally, as shown in FIG. 1, after melting the crystallized product, a low-temperature phenol stream (13) has been mixed with the molten stream (11) and introduced into the second crystallizer (33) to perform recrystallization, and in this case, the material to be melted has high melting point, and thus, more heat quantity is required than the present invention. In addition, the present application can reduce the heat quantity required in the melting process of the second heat exchanger by heating the phenol stream (13) through the first heat exchanger (23). The heat source introduced into the first heat exchanger is a low-pressure heat source during the process, where waste heat may be used. Accordingly, the present application can reduce the heat source added by using waste heat that is discarded in the entire process, thereby increasing the efficiency of the entire process and reducing energy.

In the present application, the bisphenol A concentration stream (10) is a stream containing a reaction product obtained by reacting phenol and acetone, which may be a stream in which water, acetone and other highly volatile components, such as a co-catalyst, discharged from a flasher to be described below have been completely or partially removed in advance by distillation. In one example, the bisphenol A concentration stream (10) may comprise 30 to 80 wt % of bisphenol A, 1 wt % to 60 wt % of phenol, and 5 to 40 wt % of unreacted by-products. The bisphenol A concentration stream (10) may be introduced into the first crystallizer (31) for further processing. As described above, the first crystallizer (31) can introduce the bisphenol A concentration stream containing the reaction product that phenol and acetone are reacted to crystallize bisphenol A, and discharge the adduct of crystallized bisphenol A and phenol.

In one example, the crystallizer may be a cooler. That is, the crystallization may cause supersaturation by continuously or semi-continuously removing heat from the bisphenol A concentration stream containing bisphenol A and phenol in one or more coolers for the adduct of crystallized bisphenol A and phenol to be crystallized. The adduct of crystallized bisphenol A and phenol may be in a form of a suspension. Furthermore, in addition to the cooler, the residence time necessary for supersaturation collapse and subsequent crystallization can also be provided to the crystallizer. The suspension from the crystallizer can generally be circulated through the cooler by a pump.

In addition, in an embodiments of the present application, the suspension containing the adduct of crystallized bisphenol A and phenol may be subjected to solid-liquid separation by a solid-liquid separator. In one example, the solid-liquid separator is not particularly limited as far as it is an apparatus for separating solid and liquid, and a general apparatus in the art can be used, and for example, a rotary filter or a centrifuge can be used.

In one example, the first heat exchanger (23) may further comprise a separation line (17) for separating pentane present in the phenol stream (13). The pentane may be gaseous pentane. The pentane may be partly or wholly separated through the separation line. In the present application, the separation line (17) may introduce the separated pentane into the second crystallizer (33). In an embodiment of the present application, the first exchanger (23) comprises a vent for discharging pentane, where the vent may be connected to the separation line (17) to separate pentane. In this specification, the vent may mean an air opening or a ventilating opening. The phenol stream (13) contains 2 wt % to 10 wt % or 5 wt % to 6 wt % of pentane, where if the pentane flows out to the mixed stream (12), the pressure due to vaporization may increase. Furthermore, the gas is included in the mixed stream (12) composed of solid and liquid, whereby the heat exchange efficiency may be lowered. Accordingly, as the first heat exchanger (23) comprises the separation line (17), the present application may prevent the pressure rise and increase the heat exchange efficiency.

In an embodiment of the present application, the first heat exchanger (23) can heat the phenol stream by introducing a heat source of 120° C. or lower, 115° C. or lower, 105° C. or lower, 100° C. or lower, 50° C. to 90° C. or 50° C. to 80° C. As described above, by heating the phenol stream (13) through the first heat exchanger (23), the present application can reduce the heat quantity required in the melting process of the second heat exchanger. The heat source to be introduced into the first heat exchanger may use waste heat during the process. The waste heat may be transferred by a liquid phase stream, but is not limited thereto. Accordingly, the present application can reduce the heat source to be added by using waste heat that is discarded in the entire process, thereby increasing the efficiency of the entire process and saving energy.

In one example, the second heat exchanger (21) can melt the adduct of crystallized bisphenol A and phenol by introducing steam having a pressure of 200 kPa to 500 kPa, 250 kPa to 500 kPa or 270 kPa to 480 kPa. The steam may be medium pressure steam in the process, but is not limited thereto, and low pressure steam may be used in terms of process efficiency. Also, in one example, the heat quantity of steam introduced into the second heat exchanger may be in a range of 0.8 Gcal/hr to 1.7 Gcal/hr or 1.0 Gcal/hr to 1.5 Gcal/hr. The present application can increase the efficiency of the process by controlling the heat quantity of steam to be small.

In an embodiment of the present application, as shown in FIG. 4, the apparatus for preparing bisphenol A may comprise a return line (18) for returning the adduct of crystallized bisphenol A and phenol discharged from the first solid-liquid separator (32). The return line (18) may comprise a second heat exchanger (21) and a phenol introduction port (22). That is, the second heat exchanger (21) and the phenol introduction port (22) may be installed on the return line (18). Since the return line (18) brings about the circulation of the stream of the adduct of crystallized bisphenol A and phenol, the mixed stream (12) and the molten stream (11), the position of the second heat exchanger (21) and the phenol introduction port (22) installed on the return line (18) is not particularly limited. The stream circulated through the return line (18) may be mixed again with the adduct of crystallized bisphenol A and phenol discharged from the first solid-liquid separator (32). That is, the return line (18) may mean a loop for circulating the adduct of crystallized bisphenol A and phenol discharged from the first solid-liquid separator (32) before the adduct is again introduced into the second crystallizer for recrystallization.

In one example, the production apparatus of the present application may further comprise a main reactor and a flasher. The main reactor may discharge the reaction product obtained by reacting phenol with acetone through the reaction product stream. That is, the main reactor may introduce phenol and acetone to perform the reaction, and then may discharge the reaction product to the flasher through the reaction product stream. The reaction product stream may be a mixture preferentially containing bisphenol A and water, in addition to unreacted phenol and acetone. The discharged reaction product stream is introduced into the flasher, where the flasher can separate the reaction product stream into a bisphenol A concentration stream and a phenol concentration stream. The bisphenol A concentration stream separated from the flasher can be introduced into the first crystallizer as described above. In addition, the mother liquid stream (14) separated in the first solid-liquid separator or the mother liquid stream (14) separated in a second solid-liquid separator to be described below can be introduced again into the main reactor. Also, the phenol concentration stream separated from the flasher can be gaseous, but is not limited thereto. In one example, the phenol concentration stream may be discharged to a phenol storage device. The phenol stored to the phenol storage device may be discharged to the first solid-liquid separator (32) or the second solid-liquid separator (34), which is described below, to serve as phenol for washing, or may be circulated to the main reactor.

In this specification, the term "mother liquid stream" may mean one obtained by removing substances containing bisphenol A as a main component from a component containing bisphenol A, such as a liquid phase in which the adduct of crystallized bisphenol A and phenol is separated by the solid-liquid separator after crystallization.

Stoichiometrically, the production of bisphenol A consumes 2 moles of phenol and 1 mole of acetone to produce 1 mole of bisphenol A and 1 mole of water. However, industrially, bisphenol A is prepared by reacting acetone with an excess amount of phenol in the presence of an acid catalyst. In order to obtain high purity bisphenol A from this reaction product, the reaction product is subjected to crystallization treatment to precipitate the adduct of crystallized bisphenol A and phenol, and the resulting crystal slurry is subjected to solid-liquid separation and then, phenol is removed from the recovered crystals to obtain bisphenol A. The ratio of phenol to acetone in the acid catalyzed reaction of phenol and acetone can be, for example, 5:1, 7:1, 8:1 or 9:1. The reaction is usually carried out continuously, which may be generally carried out at a temperature of 45° C. to 110° C., 50° C. to 105° C., 55° C. to 100° C. or 58° C. to 90° C. For example, as the acid catalyst, a strong inorganic acid, for example, a homogeneous and heterogeneous acid such as hydrochloric acid or sulfuric acid, or a Broensted or Lewis acid thereof can be used. Furthermore, a gel-like or porous sulfonated crosslinked polystyrene resin (acid ion exchanger) containing divinylbenzene as a crosslinking agent can be preferably used. In addition to the catalyst, thiol can generally be used as a co-catalyst, and for example, methylmercaptan can be used. As the main reactor, for example, a vertical fixed bed reactor filled with a sulfonic acid type cation exchange resin catalyst may be used, and the reaction may be continuously performed by circulating a phenol feedstock and an acetone feedstock in this reactor. After performing the reaction for a certain period of time, the operation can be stopped to clean and exchange the deteriorated catalyst. In the reaction of phenol with acetone under the acid catalyst, a reaction product stream which is a mixture containing bisphenol A and water preferentially, in addition to unreacted phenol and acetone, can be formed. Also, typical by-products of the condensation reaction, such as 2-(4-hydroxyphenyl)-2-(2-hydroxyphenyl)propane (o, p-BPA), substituted indan, hydroxyphenyl indanol, hydroxyphenyl chroman, spirobis-indane, substituted indenol, substituted xanthenes and more highly condensed compounds having 3 or more phenyl rings in the molecular backbone can be generated. In addition, additional subcomponents, such as anisole, mesityl oxide, mesitylene and diacetone alcohol can be formed as a result of the natural condensation of acetone and the reaction with impurities in the raw materials. Since unreacted feed materials such as phenol and acetone as well as secondary products such as water have a detrimental effect on suitability of bisphenol A for preparing the polymer, they can be separated by suitable methods.

In an embodiment of the present application, the apparatus for preparing bisphenol A may further comprise a second solid-liquid separator (34) in which the adduct of crystallized bisphenol A and phenol, and the mother liquid, flowing out from the second crystallizer (33) are separated and discharged. The mother liquor may be discharged into the main reactor, as described above. In addition, the crystallized product discharged from the second solid-liquid separator (34) can be melted, and the molten stream of the adduct of crystallized bisphenol A and phenol can be discharged from the second solid-liquid separator (34) and introduced into a bisphenol A refining drum (35) through a bisphenol A refining line (15). That is, the bisphenol A refining drum (35) can introduce a molten stream flowing out through the bisphenol A refining line (15). Bisphenol A may be refined in the refining drum (35) and discharged into the product stream (16).

The present application also relates to a method for preparing bisphenol A. The production method may comprise steps of: crystallizing bisphenol A through a first crystallizer (31) in a bisphenol A concentration stream (10) comprising a reaction product that phenol and acetone are reacted and discharging the adduct of crystallized bisphenol A and phenol; separating the adduct of crystallized bisphenol A and phenol in the first crystallizer (31) from the mother liquor through a first solid-liquid separator (32) and discharging it; introducing a phenol stream (13) into the adduct of crystallized bisphenol A and phenol discharged from the first solid-liquid separator (32) through a phenol introduction port (22) and discharging a mixed stream (12) of the phenol with the adduct of crystallized bisphenol A and phenol; heating the phenol stream (13) through a first heat exchanger (23) before introducing the phenol stream (13) through the phenol introduction port (22); melting the adduct of crystallized bisphenol A and phenol in the mixed stream (12) flowing out from the phenol introduction port (22) through a second heat exchanger (21) to discharge a molten stream (11); and introducing the discharged molten stream (11) to recrystallize bisphenol A through a second crystallizer (33). Furthermore, in one example, the production method may further comprise a step of separating gaseous pentane in the phenol stream through a separation line of the first heat exchanger.

In one example, the introduction of the phenol stream (13) may comprise introducing the phenol in a range of 40° C. to 100° C., 45° C. to 95° C., 50° C. to 90° C., or 55° C. to 70° C. through the phenol introduction port (22). In the temperature range, the adduct of crystallized bisphenol A and phenol can be partially melted by the phenol, and the melting point of the crystallized product can be lowered. In this specification, the term "crystallized product" may be used in the same meaning as the adduct of crystallized bisphenol A and phenol in the first crystallizer or the second crystallizer. Also, the introduction of the phenol stream (13) may comprise introducing the phenol as phenol having a flow rate of 10 ton/hr to 50 ton/hr, 20 ton/hr to 45 ton/hr or 30 ton/hr to 40 ton/hr through a phenol introduction port (22). Within the flow rate range, the melting point of the crystallized product can be efficiently lowered, thereby increasing the efficiency of the entire process.

In the conventional method for preparing bisphenol A, as shown in FIG. 1, the molten stream (11) was discharged to the second crystallizer (33), during which the molten crystallized product was mixed with the low-temperature phenol stream (13). However, in the production method according to the present application, by introducing phenol through the phenol introduction port (22) before melting of the crystallized product, the crystallized product can be mixed with the low-temperature phenol. The temperature or the flow rate of the mixed stream (12) or the molten stream (11) or the concentration of bisphenol A contained in the streams, and the like can be controlled as follows. For example, the mixed stream (12) may have a flow rate of 30 ton/hr to 200 ton/hr, 40 ton/hr to 150 ton/hr, or 50 ton/hr to 130 ton/hr. Also, the molten stream (11) may be in the range of 70° C. to 200° C., 75° C. to 180° C., 80° C. to 150° C., or 85° C. to 130° C. In addition, the molten stream (11) may comprise 20 wt % to 60 wt %, 25 wt % to 55 wt %, 30 wt % to 50 wt %, or 35 wt % to 45 wt % of bisphenol A. The production method of the present application can promote the energy efficiency of the entire process by controlling the temperature of the molten stream or the concentration of bisphenol A in the molten stream as above.

Advantageous Effects

In the process of refining bisphenol A, the present application can increase the energy efficiency of the entire process by utilizing an internal heat source.

BRIEF DESCRIPTION OF DRAWINGS

FIG. 1 is a process diagram showing a conventional apparatus for preparing bisphenol A.

FIGS. 2 to 4 are process diagrams showing apparatuses for preparing bisphenol A according to the present application.

EXPLANATION OF REFERENCE NUMERALS

10: bisphenol A concentration stream
11: molten stream
12: mixed stream
13: phenol stream
14: mother liquid stream
15: bisphenol A refining line
16: product stream
17: separation line
18: return line
21: second heat exchanger
22: phenol introduction port
23: first heat exchanger
31: first crystallizer
32: first solid-liquid separator
33: second crystallizer
34: second solid-liquid separator
35: bisphenol A refining drum

BEST MODE

Hereinafter, the apparatus and method for preparing bisphenol A will be described in detail with reference to the following Examples, but the scope of the production apparatus and the production method is not limited by the following Examples.

Example 1

Bisphenol A was prepared using the production apparatus and processes of FIG. 2. Phenol and acetone were introduced to the main reactor at a weight ratio of 9:1 and reacted at 60° C., and then water was removed from the reaction product by vaporization in a dehydrator at 178° C. and 550 mmHg, and the water-removed reaction product was supplied to the flasher. A bisphenol A concentration stream (10) excluding the phenol vaporized in the flasher is introduced into the first crystallizer (31) to produce a suspension comprising an adduct of crystallized bisphenol A and phenol. The suspension is supplied to a rotary centrifuge as the first solid-liquid separator (32), and the adduct of crystallized bisphenol A and phenol excluding the liquid phase portion separated in the rotary centrifuge is discharged. A phenol stream (13) is introduced into the discharged adduct of crystallized bisphenol A and phenol through the phenol introduction port (22). The phenol stream (13) is 58.2° C., but it is heated by a heat source of about 100° C. through the first heat exchanger (23) and introduced through the phenol introduction port (22) at a flow rate of 35 ton/hr in a state elevated to 90° C. Another phenol stream from the phenol stream (13) is introduced into the second crystallizer (33) to be described below at a flow rate of 29 ton/hr. The mixed stream (12) in which the phenol stream (13) is mixed has a flow rate of 129 ton/hr and is heated and melted with a low pressure steam of 300 kPa through the second heat exchanger (21). The melted molten stream is finally introduced into the second crystallizer (33). The molten stream is separated into the adduct of crystallized bisphenol A and phenol via the second crystallizer (33) and the second solid-liquid separator, and the adduct is discharged to the bisphenol A refining drum through the bisphenol A refining line to produce bisphenol A.

The heat quantity of the steam used in the second heat exchanger was 1.298 Gcal/hr.

Example 2

Bisphenol A was prepared using the production apparatus and processes of FIG. 4.
Phenol and acetone were introduced to the main reactor at a weight ratio of 9:1 and reacted at 60° C., and then water was removed from the reaction product by vaporization in a dehydrator at 178° C. and 550 mmHg, and the water-removed reaction product was supplied to the flasher. A bisphenol A concentration stream (10) excluding the phenol vaporized in the flasher is introduced into the first crystallizer (31) to produce a suspension comprising an adduct of crystallized bisphenol A and phenol. The suspension is supplied to a rotary centrifuge as the first solid-liquid separator (32), and the adduct of crystallized bisphenol A and phenol excluding the liquid phase portion separated in the rotary centrifuge is discharged. A phenol stream (13) is introduced into the discharged adduct of crystallized bisphenol A and phenol through the phenol introduction port (22). The phenol stream (13) is 58.2° C., but it is heated by a heat source of about 100° C. through the first heat exchanger (23) and introduced through the phenol introduction port (22) at a flow rate of 33.3 ton/hr in a state elevated to 90° C. The gaseous pentane generated in the phenol stream (13) heated by the heat source of 100° C. in the first heat exchanger (23) was introduced into the second crystallizer (33) through the vent via the separation line (17). The gaseous pentane is separated by a flow rate of 16 ton/hr at a temperature of 90° C. Another phenol stream from the phenol stream (13) is introduced into the second crystallizer (33) to be described below at a flow rate of 29 ton/hr. The mixed stream (12) in which the phenol stream (13) is mixed is heated and melted with a low pressure steam of 300 kPa through the second heat exchanger (21). The melted molten stream is circulated through the return line (18) and finally introduced into the second crystallizer (33). The molten stream is separated into the adduct of crystallized bisphenol A and phenol via the second crystallizer (33) and the second solid-liquid separator, and the adduct is discharged to the bisphenol A refining drum through the bisphenol A refining line to produce bisphenol A.

The heat quantity of the steam used in the second heat exchanger was 1.264 Gcal/hr.

Comparative Example 1

Bisphenol A was prepared using the production apparatus and processes of FIG. 1. Phenol and acetone were introduced to the main reactor at a weight ratio of 9:1 and reacted at 60° C., and then water was removed from the reaction product by vaporization in a dehydrator at 178° C. and 550 mmHg, and the water-removed reaction product was supplied to the flasher. A bisphenol A concentration stream (10) excluding the phenol vaporized in the flasher is introduced into the first crystallizer (31) to produce a suspension comprising an adduct of crystallized bisphenol A and phenol. The suspension is supplied to a rotary centrifuge as the first solid-liquid separator (32), and the adduct of crystallized bisphenol A and phenol excluding the liquid phase portion separated in the rotary centrifuge is discharged. The adduct of crystallized bisphenol A and phenol is heated and melted by medium pressure steam through the second heat exchanger (21). The melted stream is mixed with the phenol stream (13) flowing through the phenol introduction port

(22) and introduced into the second crystallizer. The phenol stream (13) flows through the phenol introduction port (22) at a temperature of 58.2° C. and a flow rate of 64 ton/hr. The mixed stream is separated into the adduct of crystallized bisphenol A and phenol via the second crystallizer and the second solid-liquid separator, and the adduct is discharged to the bisphenol A refining drum through the bisphenol A refining line to produce bisphenol A.

The heat quantity of the steam used in the second heat exchanger was 1.826 Gcal/hr.

TABLE 1

|  | Example 1 | Example 2 | Comparative Example 1 |
|---|---|---|---|
| Required heat quantity in second heat exchanger (Gcal/hr) | 1.298 | 1.264 | 1.826 |
| Temperature at second heat exchanger inlet (° C.) | 93 | 90 | 120.1 |
| Temperature at second heat exchanger outlet (° C.) | 128.5 | 127.9 | 134 |
| Flow rate at second heat exchanger outlet (ton/hr) | 60 | 60 | 233 |
| Overall heat transfer coefficient of second heat exchanger (kacl/hrcm$^2$° C.) | 864.7 | 1079.8 | 1434.5 |
| Required heat exchange area of second heat exchanger (m$^2$) | 26.9 | 20.4 | 42.24 |
| Pentane concentration of mixed stream (wt %) | 4.96 | 2.82 | 0.82 |

In the above, the second heat exchanger requires a heat quantity (Q) sufficient to melt the material from the solid-liquid separator. As a result of introducing no phenol stream, since the heat quantity required in the melting in the second heat exchanger is larger than those of Examples 1 and 2, Comparative Example 1 lowers the efficiency of the process. On the other hand, the overall heat transfer coefficient means how well the heat transfer is in the heat exchanger. Also, as the overall heat transfer coefficient is higher, the heat exchange at the desired level proceeds due to the heat exchange at a smaller heat exchange area, and thus it is efficient. In Comparative Example 1, since the phenol stream is not mixed, there is almost no gaseous pentane, so that the overall heat transfer coefficient is high, but the required heat quantity in the second heat exchanger is large and the required heat exchange area is also very high, and thus it is inefficient. In Example 1, the gaseous pentane is introduced into the mixed stream and the gas phase and the liquid phase coexist on the mixed stream, whereby the overall heat transfer coefficient is small over Example 2 and the required heat exchange area of the second heat exchanger is also large over Example 2. In the present application, the overall heat transfer coefficient and the required heat exchange area were calculated through an ASPEN EDR heat exchanger simulator.

The invention claimed is:

1. A method for preparing bisphenol A comprising steps of:
   crystallizing bisphenol A through a first crystallizer in a bisphenol A concentration stream comprising a reaction product that phenol and acetone are reacted and discharging the adduct of crystallized bisphenol A and phenol;
   separating the adduct of crystallized bisphenol A and phenol in said first crystallizer from the mother liquor through a first solid-liquid separator and discharging it;
   introducing a phenol stream into the adduct of crystallized bisphenol A and phenol discharged from said first solid-liquid separator through a phenol introduction port and discharging a mixed stream of the phenol with said adduct of crystallized bisphenol A and phenol;
   heating said phenol stream through a first heat exchanger before introducing the phenol stream through said phenol introduction port;
   melting the adduct of crystallized bisphenol A and phenol in the mixed stream flowing out from said phenol introduction port through a second heat exchanger to discharge a molten stream; and
   introducing said discharged molten stream to recrystallize bisphenol A through a second crystallizer.

2. The method for preparing bisphenol A according to claim 1, wherein the first heat exchanger comprises a separation line for separating pentane present in said phenol stream.

3. The method for preparing bisphenol A according to claim 2, further comprising a step of separating pentane in the phenol stream through a separation line of the first heat exchanger.

4. The method for preparing bisphenol A according to claim 1, wherein the introduction of the phenol stream comprises introducing phenol in a range of 40° C. to 100° C. through the phenol introduction port.

5. The method for preparing bisphenol A according to claim 1, wherein the introduction of the phenol stream comprises introducing phenol having a flow rate of 10 ton/hr to 50 ton/hr through the phenol introduction port.

6. The method for preparing bisphenol A according to claim 1, wherein the mixed stream is discharged from the phenol introduction port at a flow rate of 30 to 200 ton/hr.

7. The method for preparing bisphenol A according to claim 1, wherein the molten stream is in a range of from 70° C. to 200° C.

8. The method for preparing bisphenol A according to claim 1, wherein the molten stream comprises 20 wt % to 60 wt % of bisphenol A.

9. The method for preparing bisphenol A according to claim 2, wherein the separation line introduces separated pentane into the second crystallizer.

10. The method for preparing bisphenol A according to claim 1, wherein the first heat exchanger heats the phenol stream by introducing a heat source of 120° C. or lower.

11. The method for preparing bisphenol A according to claim 9, wherein the first heat exchanger comprises a vent for discharging pentane and said vent is connected to the separation line to separate pentane.

12. The method for preparing bisphenol A according to claim 1, wherein the second heat exchanger melts the adduct of crystallized bisphenol A and phenol by introducing steam having a pressure of 200 kPa to 500 kPa.

13. The method for preparing bisphenol A according to claim 1, comprising returning the adduct of crystallized bisphenol A and phenol discharged from the first solid-liquid separator via a return line, wherein said return line comprises the second heat exchanger and the phenol introduction port, and a stream flowing out through said return line is again mixed with the adduct of crystallized bisphenol A and phenol discharged from the first solid-liquid separator.

14. The method for preparing bisphenol A according to claim 1, further comprising reacting phenol and acetone in a main reactor, discharging a reaction product from the main reactor via a reaction product stream, and introducing said reaction product stream into a flasher, and separating the reaction product stream into a bisphenol A concentration stream and a phenol concentration stream, wherein the bisphenol A concentration stream separated from said flasher is introduced into the first crystallizer and the mother liquid stream separated in the first solid-liquid separator flows out to said main reactor.

15. The method for preparing bisphenol A according to claim 1, further comprising separating the adduct of crystallized bisphenol A and phenol, and the mother liquid, flowing out from the second crystallizer in a second solid-liquid separator.

16. The method for preparing bisphenol A according to claim 15, further comprising discharging the molten stream of the adduct of crystallized bisphenol A and phenol discharged from the second solid-liquid separator via a bisphenol A refining line.

17. The method for preparing bisphenol A according to claim 16, further comprising introducing a molten stream flowing out through the bisphenol A refining line into a bisphenol A refining drum.

* * * * *